United States Patent [19]

Monnier et al.

[11] Patent Number: 5,081,096
[45] Date of Patent: Jan. 14, 1992

[54] EPOXIDATION CATALYST

[75] Inventors: John R. Monnier, Fairport; Peter J. Muehlbauer, Spencerport, both of N.Y.

[73] Assignee: Eastman Kodak Company, Rochester, N.Y.

[21] Appl. No.: 557,359

[22] Filed: Jul. 25, 1990

[51] Int. Cl.$^5$ .............. B01J 21/04; B01J 23/04; B01J 23/50
[52] U.S. Cl. ..................... 502/348; 502/347
[58] Field of Search ............... 502/347, 348

[56] References Cited

U.S. PATENT DOCUMENTS

| | | | |
|---|---|---|---|
| 2,773,844 | 12/1956 | Carlson et al. | 252/463 |
| 3,575,888 | 4/1971 | Long | 252/476 |
| 3,702,259 | 11/1972 | Nielsen | 117/37 R |
| 3,962,136 | 6/1976 | Nielsen et al. | 252/454 |
| 4,007,135 | 2/1977 | Hayden et al. | 502/347 X |
| 4,010,115 | 3/1977 | Nielsen et al. | 252/454 |
| 4,012,425 | 3/1977 | Nielsen et al. | 260/348.5 R |
| 4,033,903 | 7/1977 | Maxwell | 502/347 |
| 4,356,312 | 10/1982 | Nielsen et al. | 549/534 |
| 4,419,276 | 12/1983 | Bhasin et al. | 502/347 |

Primary Examiner—W. J. Shine
Attorney, Agent, or Firm—J. Frederick Thomsen; William P. Heath, Jr.

[57] ABSTRACT

Disclosed is a novel catalyst composition comprising a catalyst support material having deposited thereon elemental silver and a promoter selected from potassium, rubidium and cesium which are obtained by treating a catalyst precursor comprising a porous catalyst support material having deposited thereon a silver compound and a promoter selected from compounds of potassium, rubidium and cesium, with a gas comprising (i) hydrogen or (ii) an inert gas containing at least about 4 volume percent hydrogen at elevated temperatures. The disclosed catalysts are particularly useful in the partial oxidation of butadiene to produce 1,2-epoxy-3-butene.

12 Claims, No Drawings

EPOXIDATION CATALYST

This invention pertains to novel supported silver catalysts useful for the epoxidation of ethylenically-unsaturated compounds such as olefins and vinyl-substituted compounds and to processes for the preparation of the catalysts. More particularly, this invention pertains to supported, promoted silver catalysts which are especially useful for the monoepoxidation of dienes such as butadiene.

Many of the supported silver catalysts and the processes for the preparation thereof described in the prior art are used in the epoxidation or partial oxidation of ethylene to produce ethylene oxide. The preparation of these known catalysts involves, in general, the deposition on a catalyst support material of a silver compound and, optionally, one or more other inorganic and/or organo-metallic compounds, either separately or simultaneously with the deposition of the silver compound. The resulting silver-bearing support material then is subjected to various thermal treatments to convert the silver compound to the active metallic silver. According to the prior art, the final thermal treatment is carried out in the presence of a reducing agent. Thus, U.S. Pat. No. 2,773,844 discloses the preparation of a supported, silver catalyst by the steps of (1) impregnating an alumina support material with silver nitrate, (2) drying the support and heating it at 300° C. in a stream of nitrogen, and (3) heating the catalyst at 260° C. in a stream of hydrogen and nitrogen until substantially all of the silver nitrate was converted to metallic silver. U.S. Pat. No. 3,702,259 discloses treating a silver nitrate-bearing support material with 0.6 volume percent hydrogen at 220° C. for 8 hours and 10 volume percent hydrogen for 1 hour. Another chemical reduction technique is disclosed in U.S. Pat. No. 3,575,888 wherein a silver nitrate-impregnated catalyst support material is contacted with an anhydrous solution of a reducing agent, e.g., an ethanol solution of hydrazine, hydroxylamine, formaldehyde and acetaldehyde, at temperatures in the range of $-10°$ to $55°$ C.

The more recent patent literature exemplifies the conversion of a silver compound deposited on a support material to metallic silver by means of a thermal decomposition-reduction step wherein an amine-solubilized silver carboxylate is heated at 100° to 375° C., preferably from 125° to 325° C., for a time sufficient, typically 0.5 to 8 hours, to decompose the silver salt. More specifically, U.S. Pat. Nos. 3,962,136, 4,010,115, 4,012,425 and 4,356,312 disclose impregnating a catalyst support material with an aqueous solution of an ethylene diamine-silver oxalate complex and ethanolamine. The wet, impregnated catalyst support is then heated at 290° C. for 3 hours in a forced air oven to dry the catalyst and to reduce the silver salt to silver metal.

Certain of the above-cited patents, i.e., U.S. Pat. Nos. 3,962,136, 4,010,115, 4,012,425 and 4,356,312, disclose that the presence of certain alkali metal compounds, preferably potassium, rubidium, and especially cesium compounds, on a supported silver catalyst improves the selectivity of the catalyst in the partial oxidation of ethylene to ethylene oxide. These patents disclose that the alkali metal compounds may be deposited on the catalyst support material either subsequent to or simultaneously with the deposition of the silver compound.

We have discovered that the activity/selectivity of a catalyst comprising a porous catalyst support material having deposited thereon metallic silver and an alkali metal is improved, relative to known catalysts, when the catalyst precursor comprising a porous catalyst support material having deposited thereon a silver compound e.g., an inorganic silver salt, and an alkali metal compound is heated in the presence of hydrogen under certain conditions. Our invention thus pertains to the preparation of a supported silver epoxidation catalyst by intimately contacting at a temperature of about 170° to 600° C. a catalyst precursor comprising a porous catalyst support material having deposited thereon a silver compound and a promoter selected from potassium, rubidium or cesium salts, with a gas comprising (i) hydrogen or (ii) an inert gas containing at least about 4 volume percent hydrogen. The catalysts provided in accordance with our invention are particularly useful for the monoepoxidation of 1,3-butadiene to obtain 1,2-epoxy-3-butene and exhibit improved activity in terms of conversion of the butadiene.

The support component of the catalysts which is obtained in accordance with our invention may be selected from the large number of conventional, porous, refractory catalyst carriers or support materials which are essentially inert in the presence of the ethylenically unsaturated compound and oxygen-containing gas feeds and the products in the processes in which the catalysts are employed. Such conventional materials may be of natural or synthetic origin and preferably are of a macroporous structure, that is, a structure having a surface area below about 10 $m^2/g$. These support materials typically have an apparent porosity of greater than 20%. Supports having a siliceous and/or aluminous composition are, in general, preferred. Specific examples of suitable supports are the aluminum oxides (including the materials sold under the trade name "Alundum"), charcoal, pumice, magnesia, zirconia, kieselguhr, fuller's earth, silicon carbide, porous agglomerates comprising silicon and/or silicon carbide, silica, magnesia, selected clays, artificial and natural zeolites and ceramics. Refractory supports particularly useful in the preparation of catalysts in accordance with this invention comprise the aluminous materials, in particular those containing alpha alumina. In the case of alpha alumina-containing supports, preference is given to those having a specific surface area as measured by the B.E.T. method of from about 0.03 to 10 $m^2/g$ and an apparent porosity as measured by conventional mercury or water absorption techniques of from about 25 to about 50% by volume. The B.E.T. method for determining specific surface area is described in detail in Brunauer, S., Emmet, P. H., and Teller, E., J. Am. Chem. Soc., 60, 309-16 (1938).

The following materials are specific examples of the catalyst supports which may be used.

I. Norton SN-06595, a fluidizable powder having a surface area of 0.26 $m^2/g$, a total pore volume of 0.675 cc (Hg)/gm, median pore diameter 19$\mu$, a packing density of 0.98 $g/cm^3$, and a chemical composition (weight percent) of: $Al_2O_3$—84.7, $SiO_2$—13.4, $Fe_2O_3$—0.21, $TiO_2$—0.47, CaO—0.21, MgO—0.12, $Na_2O$—0.15, $K_2O$—0.26).

II. Norton SN-08228, 0.1875 inch pellets with a surface area of 0.26 $m^2/g$, a total pore volume of 0.23 cc(Hg)/gm, median pore diameter of 19$\mu$, a packing density of 0.90 $g/cm^3$, and a chemical composition (weight percent) of: alumina—84.7, $SiO_2$—13.4, $Fe_2O_3$—0.21, $TiO_2$—0.47, CaO—0.21, MgO—0.12, $Na_2O$—0.15, $K_2O$—0.26.

III. Norton SA-5252, 0.1875 inch spheres with a surface area of 0.39 m$^2$/g, a total pore volume of 0.36 cc(Hg)/gm, median pore diameter of 5.4μ, a packing density of 0.94 g/cm$^3$ and a chemical composition (weight percent) as follows: Al$_2$O$_3$—93.1, SiO$_2$—5.6, Fe$_2$O$_3$—0.3, TiO$_2$—0.1, CaO—0.1, MgO—0.3, Na$_2$O—0.1, K$_2$O—0.1.

IV. Norton 5552 Alumina Rings—0.25 inch rings having a surface area of 0.43 m$^2$/g, a total pore volume of 0.37 cc (Hg)/gm, a median pore diameter of 7μ, a packing density of 0.80 g/cm$^3$, and a chemical composition (weight percent) of: Al$_2$O$_3$—93.1, SiO$_2$—5.6, Fe$_2$O$_3$—0.3, TiO$_2$—0.1, CaO—0.1, MgO—0.3, Na$_2$O—0.1, K$_2$O—0.1.

V. Norton SN-82501, 0.1875 inch spheres having a surface area of 0.13 m$^2$/g, a total pore volume of 0.37 cc(Hg)/gm, a median pore diameter of 32.5μ, a packing density of 0.88 g/cm$^3$, and a chemical composition (weight percent) of: Al$_2$O$_3$—85.0, SiO$_2$—12.0, and the remaining 3% as Fe$_2$O$_3$, TiO$_2$, CaO, MgO, Na$_2$O and K$_2$O.

Although not preferred, other support materials which may be used include zinc oxide, e.g., having a surface area of about 3.9 m$^2$/g and a particle size of about 75-50μ; titania, e.g., having a surface area of about 0.5 m$^2$/g and a particle size of about 40-75μ; calcium oxide; silica, e.g., having a surface area of about 0.18 m$^2$/g and a particle size of about 75-250μ; barium oxide, e.g., having a surface area of about 1 m$^2$/g and a particle size of 40-75μ; boron nitride; silicon nitride; and silicon carbide.

A preferred class of support materials comprise low surface area, fused, alpha alumina supports which have relatively uniform pore diameters and are more fully characterized by having (1) B.E.T. specific surface areas of from about 0.1 m$^2$/g to about 2.0 m$^2$/g, preferably about 0.3 m$^2$/g, and (2) apparent porosities of from about 42% to about 60%, preferably from about 46% to about 58%. Specific examples of these most advantageous supports are described hereinabove.

The actual physical form of the catalyst support is not particularly important. While the form of the catalyst support has little effect on catalyst activity, practical considerations such as ease of heat transfer, mass transfer, pressure drop due to fluid flow restrictions, efficiency of gas-liquid-solid contacting, catalyst durability, and the like make the use of defined shapes such as spheres, pellets, extrudates, rings, saddles, and the like preferred. Conventional commercial fixed-bed reactors used in the epoxidation of ethylenically-unsaturated compounds typically are in the form of a plurality of parallel elongated tubes (in a suitable shell) approximately 1 to 2 inches in diameter and 24 to 45 feet long filled with catalyst. In such reactors, it is desirable to employ a support formed into a rounded shape, such as, for example, spheres, pellets, rings, tablets, and the like, having diameters of from about 0.1 inch to about 0.8 inch.

The catalyst precursors employed in the process of our invention may be prepared employing techniques well known to those of skill in the art, such as, for example, by precipitation of suitable silver and alkali metal compounds on the support, by impregnation, by coprecipitation of the silver and alkali metal compounds and the support material, by grinding together the support material and the silver and alkali metal compounds in particulate form and the like. The order in which the alkali metal promoter is incorporated onto the support material is not critical, e.g., the support may be contacted with a silver source, then promoter, or the support may be contacted with an alkali metal compound, then a silver compound, or the support material may be contacted simultaneously with both an alkali metal compound and a silver compound.

The silver compound employed in the preparation of the catalyst precursor is not critical. Typically, the preparation of the catalyst precursor comprises impregnating the support material with a solution of a silver compound in water, an alcohol, a glycol ether, or a mixture thereof. Exemplary compounds are silver nitrate, silver oxalate, silver acetate, and the like. Those skilled in the art recognize that certain organic silver compounds require the addition of ammonia or an amine in order to solubilize the organic silver compound in an aqueous medium; thus, the use of such solvation-promoting additives is contemplated in the practice of the present invention.

The improved catalysts provided by the present invention may contain about 0.5 to 50 weight percent, calculated as elemental or metallic silver and based on the total weight of active catalyst. Preferably, the loading level of silver on the support is within the range of about 1 up to 30 weight percent elemental silver, with loading levels in the range of about 2 to 20 weight percent being most preferred. The silver typically is present in the form of uniformly-spaced, discontinuous, adherent, substantially hemispherical, discrete particles having an essentially uniform diameter of about 1000 to 50,000 A. Catalysts bearing silver particles less than about 1000 A give inferior catalytic results whereas silver particles larger than about 50,000 A do not appear as uniformly-spaced, discontinuous particles but appear to give a continuous layer of inter-grown crystals which results in a catalyst having inferior activity due to loss of silver surface area.

The alkali metal or metals, i.e., potassium, rubidium, and/or cesium, are present on the active catalysts prepared in accordance with our invention in the form of their cations, rather than as the extremely active, free alkali metals. Silver, on the other hand, is present on the finished catalysts as silver metal. The exact form of the alkali metal on the finished catalyst is not known. However, the heat treatment given to the impregnated support in the reduction of the silver salts to metallic silver most likely converts the alkali metal salts to an oxide or oxidic compound. The amount of alkali metal oxide compound present on the catalyst support is expressed herein as the weight percent, based on the total weight of the catalyst, of the alkali metal rather than the oxide.

The amount of the alkali metal (or metals) present on the catalyst surface may vary substantially depending, for example, on the particular alkali metal or metals employed, the particular support material employed, the amount of silver on the catalyst and/or the surface area thereof, the use for which the catalyst is designed and similar factors. Generally, the amount of alkali metal on the active catalyst is in the range of about 0.001 to 10 weight percent, based on the total weight of the active catalyst with amounts in the range of about 0.01 to 2 weight percent (same basis) being more common. For catalysts intended for the monoepoxidation of butadiene, the amount of the alkali metal, especially cesium, present on the surface of the support material preferably is about 0.01 to 0.2 weight percent.

The amounts of the alkali metals, i.e., potassium, rubidium and/or cesium, deposited are not necessarily the total amounts of these metals present in the catalysts. They are the amounts of the alkali metals which are present on the surface of the catalyst and which are intentionally added to the catalysts. It is not unusual for substantial amounts, often up to about 10,000 ppm by weight of an alkali metal (usually potassium) to be present within the porous support due to the use of support materials containing naturally occurring alkali metals or alkali metal addition during support manufacture. These amounts of alkali metal present in the support in non-leachable form, rather than on the surface, do not appear to contribute to the improved performance of catalysts in accord with this invention and are neglected in determination of alkali metal concentrations.

The catalyst precursor comprising a catalyst support material having the silver and alkali metal compounds deposited thereon as described hereinabove is converted to an active catalyst by intimately contacting the precursor with a gas comprising (i) hydrogen, or (ii) an inert gas containing at least about 4 volume percent hydrogen at a temperature of about 170° to 600° C. whereby the silver compound is reduced to elemental silver and the alkali metal compound is converted to alkali oxides. The particular conditions employed in the high temperature hydrogen treatment can vary substantially since the hydrogen concentration and temperature as well as contact times are interdependent.

We have found that to obtain a highly active epoxidation catalyst, the reduction should proceed in a vigorous, fast manner by the use of an appropriate balance of temperature, hydrogen concentration in the gas, and flow rates of the reduction gas. Generally, higher concentrations of hydrogen require lower temperatures and contact times. The effectiveness of the reduction also is affected by the flow rate of the reducing gas. Thus, when a fixed bed of the catalyst precursor is subjected to the gas treatment as described above, the gas hourly space velocity (GHSV; volume of gas fed per hour per volume of catalyst precursor being treated) of the hydrogen-containing gas is in the range of about 10 to 10,000, with the optimum GHSV depending on the hydrogen content of the gas, the temperature employed and the physical form of the support material. Although we do not wish to be bound by any particular theory with respect to the effectiveness of the reduction, it appears that the formation of a catalyst of superior activity requires that the reduction occur as a wavefront with the reduction of the silver compound occurring substantially in a quantitative manner at the leading edge of the hydrogen front. For example, we have found that if the flow rate of the gas is too fast, the reduction does not occur as a moving gradient but is spread out over a large bed distance, resulting in a catalyst which does not exhibit optimum activity. Thus, it is believed that by the use of the appropriate combination of hydrogen concentration and gas flow rates, the reduction of the silver compound occurs quantitatively, or substantially quantitatively, with substantially complete hydrogen consumption at the wavefront as it moves through the catalyst bed. Temperatures in excess of 600° C. should be avoided during the gas treatment of the catalyst precursor since such can cause sintering of the elemental silver resulting in a catalyst having poor activity. Preferably, the gas treatment is carried out at temperatures not exceeding about 550° C.

The gas treatment described above preferably is carried out at an initial temperature of from about 170° to 500° C. using a gas comprising an inert gas containing about 4 to 50 volume percent hydrogen. When using these temperatures and hydrogen concentration, the GHSV of the gas typically will be about 10 to 5000. The gas treatment preferably is commenced at a temperature of about 170° C. and the temperature of the bed of catalyst precursor is allowed to rise to at least 240° C., preferably to at least 350° C., by the heat generated by the reduction.

Examples of the inert gases which may be used in the gas treatment include nitrogen, helium, argon, carbon dioxide, methane, or a mixture thereof. Prior to contacting the catalyst precursor with hydrogen, an inert gas may be passed over the precursor at elevated temperatures. For example, an inert gas may be passed over the catalyst precursor for 0.1 to 1 hour or longer at a gas hourly space velocity in the range of 10 to 10,000 and at temperatures of 100° to 350° C., preferably 200° to 300° C. Immediately following this pre-reduction "thermal soak", the gas feed may be changed to a hydrogen-containing gas with reduction of the silver compound commencing at about 170° C. or at the thermal soak temperature, which ever is higher. Normally, such a pre-reduction soak does not affect materially the activity/selectivity of the final catalyst.

The apparatus used in the gas treatment step is not important provided that the reduction of the silver compound can be achieved as described above. For example, such apparatus may comprise a cylindrical vessel provided with means for maintaining the catalyst precursor in a fixed position and for providing uniform distribution of the gas. Such apparatus may consist of one or more reactor tubes in which the catalyst, after reduction, may be used in the epoxidation of an ethylenically-unsaturated compound such as butadiene. Alternatively, the reduction apparatus may comprise an independent cylindrical vessel designed to operate solely as a reduction device.

The process of the present invention may be carried out at pressures in the range of about 0.5 to 50 bar although the practice of the process at ambient pressure or pressures slightly above ambient give catalysts which exhibit excellent activity in the partial oxidation of butadiene. Upon the completion of the hydrogen gas treatment, the catalysts thus obtained may be subjected to an extended period of gas treatment at elevated temperatures to permit the catalyst bed to achieve thermal and chemical equilibrium by removing the last traces of reduction products, e.g., water and nitrogen oxides, from the catalyst bed. This "thermal soak" typically is performed at temperatures in the range of about 300° to 400° C. using gas flow rates similar to those used in the hydrogen gas treatment, e.g. 10 to 5000 GHSV. The gas used may be the same as that used in the hydrogen gas treatment or may be an inert gas such as nitrogen.

Prior to the gas treatment/reduction procedure described hereinabove, the catalyst precursor may be subjected to a calcination procedure wherein a gas is passed over or through the catalyst precursor at a temperature of about 250° to 350° C. for about 2 to 4 hours using gas hourly space velocities in the range of about 10 to 5000. During the calcination, the silver compound is more evenly distributed in the pores and on the surface of the catalyst support material. The gas used in the calcination procedure is not critical and may be selected from air, oxygen-depleted air, inert gases such as nitrogen, argon, helium, etc. or any mixture thereof. Although it is believed not to be critical, the use of the calcination procedure is preferred since it provides a more uniform distribution of the silver and alkali metal compounds over the interior and exterior surfaces of the support material. Preferred calcination conditions comprise a temperatures of about 300° C., times of about 2 to 4 hours and gas hourly space velocities of about 50 to 500.

Our novel process and the improved catalysts obtained therefrom are further illustrated by the following examples. The catalyst precursors used in the examples are prepared by the following procedure:

REFERENCE EXAMPLE 1

Silver nitrate (140.0 g) is added to a solution of cesium chloride (0.4375 g) in distilled water (300 mL) in a 2 L, pear-shaped, fluted flask which is placed on a rotary evaporator at 50° C. and tumbled at 20–30 revolutions per minute at atmospheric pressure to dissolve the silver nitrate. After the silver nitrate is completely dissolved, alumina rings (500 g, Norton 5552 Alumina described hereinabove) are added to the flask which is then tumbled at 20–30 rpm on the rotary evaporator for about 5 minutes to ensure complete wetting of all the rings. The temperature of the flask is increased to 60° C. and the pressure is reduced. When the water begins to boil at reduced pressure, the vacuum is released several times to ensure complete wetting within the pores of the alumina rings. The water then is removed at about 60° C. and about 0.01 to 500 torr over a period of from 0.5 to 1.0 hours.

When the rate of water collection in the rotary evaporator slows to about 1 drop every 10 seconds, the impregnated support is transferred to a tumble drying basket fabricated of perforated steel and having a diameter of 10 inches, a length of 10 inches and 4 2-inch interior baffles to ensure adequate tumbling of the impregnated support. The drying basket is placed in a forced air oven preheated to 170° C. and the impregnated support is tumble dried at 5–10 rpm for 90 minutes. The resulting catalyst precursor may be stored for future use in the gas treatment/reduction process of our invention or it may be subjected to the calcination procedure described in the following example.

REFERENCE EXAMPLE 2

The catalyst precursor prepared as described may be calcined in a calcination vessel equipped with a gas inlet connected to a gas dispersion frit covering the bottom of the container. The catalyst precursor is placed above the glass frit and the vessel is positioned in a programmable furnace and connected to a calibrated flowmeter which supplies air at a gas hourly space velocity of 5 to 1000. The catalyst precursor is heated to 300° C. at a rate of 2° to about 10° C. per minute, held at 300° C. for 300 minutes and then cooled to room temperature over a period of about 30 minutes.

REDUCTION PROCEDURE

Unless specified otherwise, the reductions described in the following examples are carried out in a vertically-mounted Pyrex glass tube 3 feet in length having an interior diameter of 1.5 inches. The catalyst precursor (typically 300–350 g) is placed in the tube and is held in position with a sintered stainless steel frit. The catalyst precursor charge (typically 10–14 inches deep) is maintained in the middle portion of the Pyrex glass tube. Stainless steel-clad thermocouples are placed in the top, middle and bottom of the catalyst precursor bed. The furnace enclosing the reduction train is vertically-hinged with 3 separately controlled heating zones to prevent the formation of thermal gradients (due to uneven heating) in the catalyst bed. The predetermined flows of hydrogen and nitrogen are supplied from calibrated flowmeters and the gases are blended in a manifold before entering the top of the reduction tube.

During reduction, the temperatures of the catalyst precursor bed are monitored by a data logging system interfaced with the 3 thermocouples in the bed. The onset of reduction is marked by the appearance, and the completion of reduction by the disappearance, of water/nitrogen oxides (brown coloration) in the gas exit stream at the bottom of the tube. Reduction also is monitored by temperature increases (exotherms) resulting from the exothermic reaction which occurs during the reduction as indicated by the thermocouples embedded in the catalyst. When reduction is complete, the active catalyst optionally is subjected to a 1–2 hour thermal treatment at 350° C. in the nitrogen/hydrogen composition used in the reduction. After the reduction or thermal treatment, the activated catalyst is cooled to room temperature.

REFERENCE EXAMPLE 3

The catalysts prepared as described herein are evaluated in the monoepoxidation of butadiene at steady state conditions using a one atmosphere, single-pass flow reactor. The reactor tube is fabricated from Pyrex glass tubing and is 12 inches in length with an inside diameter of 0.75 inches. The catalyst charge (2–8 g) is held in place in the middle portion of the reactor tube by means of a Pyrex glass frit or glass wool. A Chromel/Alumel alloy thermocouple sheathed in stainless steel is embedded within the catalyst bed to measure reaction temperature. The reactor is heated by means of a tube furnace equipped with a proportional band controller.

The helium diluent and butadiene and oxygen are fed to the reactor in a helium:butadiene:oxygen volume ratio of 4:1:1 at a gas hourly space velocity of 2200 using mass flow controllers, which permit highly accurate and reproducible flow rates of helium, butadiene and oxygen regardless of pressure changes from the supply cylinders or the reactor system downstream from the controllers. The butadiene oxidations are carried out at 225° C.

Analyses of the reaction products and feed compositions are performed using an in-line gas sampling loop connected directly to the inlet of a Varian 3760 gas chromatograph. Both thermal conductivity (TC) and flame ionization (FI) detectors [(connected in series below the packed Chromosorb 101 column (8 ft. by 2 mm id Pyrex glass capillary column)] are used to analyze all of the reaction products. The TC detector gave quantitative analyses for oxygen, carbon dioxide, water and formaldehyde (if present), while the FI detector is used for organic molecules such as butadiene, butadiene monoxide, crotonaldehyde, 2,5-dihydrofuran, furan and acrolein. In practice, however, usually only the selective epoxidation product and olefin feedstock are present as organic molecules. Further, by means of a switching valve, it is possible to divert the feed stream through the in-line sample loop prior to passage over the catalyst. In this way, quantitative analysis of the feed stream and comparison to the corresponding data from the reactor effluent are possible, thereby providing very accurate measurements of both conversion levels and product selectivities. Output from both the TC and FI detectors are integrated using computing integrators which are programmed to give both absolute quantities and rates of formation. All reactor exit lines are heated and maintained at 125°-140° C. to prevent product condensation.

The GC analysis is performed using the following temperature programming schedule: an initial temperature of 100° C. is held for 5 minutes, followed by a temperature program rate of +10° C./minute up to a final temperature of 200° C. which is then held for 7 minutes. The helium GC carrier rate is 20 mL/min.

EXAMPLES 1-5

Five portions (350 g) of catalyst precursor prepared as described in Reference Examples 1 and 2 are heated in the presence of varying concentrations of hydrogen in nitrogen using different gas flow rates according to the reduction procedure set forth above. The hydrogen-containing reduction gas is passed over each portion of catalyst precursor while the bed is heated. The onset or commencement of reduction occurs at about 170° C. for each of the 5 experiments. The highest temperature reached during the 5 experiments varies due to the increased exothermicity resulting from using progressively higher concentrations of hydrogen in the reduction gas.

Each of the five catalysts contained 12 weight percent elemental silver and 0.10 weight percent cesium (both percentages based on the total weight of the finished catalyst) and are evaluated in the monoepoxidation of butadiene according to the procedure described in Reference Example 3. The volume percent hydrogen in the hydrogen/nitrogen reduction gas (%H$_2$), the flow rate of the reduction gas (GHSV), the reduction time (Time, minutes) and the highest temperature (Temp, max, °C.) recorded by any of the three thermocouples during the preparation of each of the five catalysts are shown in Table I. Also shown in Table I are the mole percent conversion (Conv) of butadiene defined as:

$$\frac{\text{Moles butadiene converted to products}}{\text{Moles butadiene fed}} \times 100$$

and the percent selectivity to 1,2-epoxy-3-butene defined as:

$$\frac{\text{Moles butadiene converted to 1,2-epoxy-3-butene}}{\text{Moles butadiene converted to total products}} \times 100$$

TABLE I

| Example | % H$_2$ | GHSV | Time | Temp, max | Conv | Select |
|---|---|---|---|---|---|---|
| 1 | 5 | 360 | 90 | 410 | 12.5 | 95.5 |
| 2 | 15 | 410 | 38 | 470 | 9.3 | 93.0 |
| 3 | 25 | 410 | 25 | 490 | 10.4 | 94.4 |
| 4 | 33 | 460 | 18 | 510 | 12.0 | 93.5 |
| 5 | 50 | 410 | 13 | 575 | 12.5 | 94.6 |

EXAMPLES 6 AND 7 AND COMPARATIVE EXAMPLE 1

The reduction procedure described in Examples 1-5 is repeated with three portions (8 g each) of catalyst precursor using the same oxidation apparatus as is described in Reference Example 3. Each of the three catalysts obtained contained 12.0 weight percent elemental silver and 0.10 weight percent cesium based on the total weight of the finished catalyst. The volume percent hydrogen in the hydrogen/nitrogen reduction gas (%H$_2$), the flow rate of the reduction gas (GHSV), the highest temperature (Temp, max, °C.) recorded during the preparation of each of the three catalysts, the mole percent conversion of butadiene and the percent selectivity to epoxybutene, as defined above, are set forth in Table II.

TABLE II

| Example | % H$_2$ | GHSV | Temp, max | Conv | Select |
|---|---|---|---|---|---|
| 6 | 5 | 700 | 330 | 7.1 | 97 |
| 7 | 20 | 700 | 450 | 13.5 | 95 |
| C-1 | 5 | 4700 | 300 | 0.3 | 40 |

The results obtained from Examples 6 and 7 and Comparative Example 1 show that the use of high flow rates of reduction gas, particularly reduction gas which contains a low concentration of hydrogen, gives a catalyst having poor activity and selectivity in the oxidation of butadiene.

EXAMPLE 8 AND COMPARATIVE EXAMPLE 2

The procedure of Examples 1-5 is repeated for Example 8 and the procedure for Comparative Example 2 is essentially the same as Example 8 except that the catalyst precursor is heated at 450° C. in a gas stream consisting only of nitrogen. Each of the catalysts obtained contained 12.0 weight percent elemental silver and 0.10 weight percent cesium based on the total weight of the finished catalyst. The volume percent hydrogen in the hydrogen/nitrogen reduction gas (%H$_2$), the flow rate of the gas (GHSV), the mole percent conversion of butadiene and the percent selectivity to epoxybutene, as defined above, are set forth in Table III.

TABLE III

| Example | % H$_2$ | GHSV | Conv | Select |
|---|---|---|---|---|
| 8 | 20 | 600 | 13.5 | 96 |
| C-2 | 0 | 600 | 5.0 | 98 |

EXAMPLE 9 AND COMPARATIVE EXAMPLE 3

The procedure of Examples 1-5 is repeated using 300-350 g portions of catalyst precursor. After the actual reduction period of 20 minutes, the catalyst of Example 9 is given an additional thermal soak at 300° C. for 1 hour in a stream of 20 volume percent hydrogen in nitrogen whereas the catalyst of Comparative Example is not. Each of the catalysts obtained contained 12.0 weight percent elemental silver and 0.10 weight percent cesium based on the total weight of the finished catalyst. The volume percent hydrogen in the hydrogen/nitrogen reduction gas (%H$_2$), the flow rate of the reduction gas (GHSV), the reduction time (Time, minutes) and the highest temperature (Temp, max, °C.) recorded by any of the three thermocouples during the preparation of each of the three catalysts are shown in Table IV wherein the mole percent conversion of butadiene and the percent selectivity to epoxybutene, as defined above, also are set forth.

TABLE IV

| Example | % H$_2$ | GHSV | Time | Temp. max | Conv | Select |
|---|---|---|---|---|---|---|
| 9 | 20 | 600 | 20 | 450 | 13.8 | 96 |

TABLE IV-continued

| Example | % H₂ | GHSV | Time | Temp. max | Conv | Select |
|---|---|---|---|---|---|---|
| C-3 | 1 | 600 | 720 | 240 | 2.0 | 96 |

Comparative Example C-3 demonstrates that the use of a reduction gas containing only 1 volume percent hydrogen gives a markedly inferior catalyst.

EXAMPLES 10-13

The procedure of Examples 1-5 is repeated except that in each of Examples 10, 11 and 12 the catalyst precursor is given a pre-reduction thermal soak by passing nitrogen over the catalyst for 1 hour at a gas hourly space velocity of 400° at 250° C. (Example 10) or 300° C. (Examples 11 and 12). At the end of the 1 hour period, hydrogen is added to the nitrogen gas feed and reduction of the silver nitrate commences at the temperature of the thermal soak, i.e., at 250° or 300° C. In Example 13, the pre-reduction soak procedure is not employed. Each of the catalysts obtained contained 12.0 weight percent elemental silver and 0.10 weight percent cesium based on the total weight of the finished catalyst. The volume percent hydrogen in the final hydrogen/nitrogen reduction gas (%H₂), the flow rate of the reduction gas (GHSV), the reduction time (Time, minutes) and the highest temperature (Temp, max, °C.) recorded by any of the three thermocouples during the preparation of each of the three catalysts are shown in Table V. The mole percent conversion of butadiene and the percent selectivity to epoxybutene, as defined above, achieved using each of the catalysts in the above-described butadiene oxidation procedure also are given in Table V.

TABLE V

| Example | % H₂ | GHSV | Time | Temp. max | Conv | Select |
|---|---|---|---|---|---|---|
| 10 | 20 | 600 | 22 | 400 | 10.0 | 95 |
| 11 | 20 | 600 | 22 | 450 | 11.7 | 95 |
| 12 | 50 | 600 | 10 | 450 | 13.9 | 96 |
| 13 | 20 | 600 | 25 | 400 | 11.5 | 96 |

COMPARATIVE EXAMPLE 4

Using the general procedure of Reference Example 1, alumina rings (25 g) are impregnated using a solution prepared by adding silver oxalate (6.27 g), along with sufficient ammonium hydroxide to dissolve the silver oxalate, to a solution of cesium chloride (0.0219 g) in distilled water (5 mL). The liquid is removed under vacuum as described previously. The catalyst is activated in the programmable furnace as described in Reference Example 2 by heating it from 120° to 250° C. over a period of approximately 4 hours and then is cooled. The catalyst obtained contained 11.7 weight percent elemental silver and 0.07 weight percent cesium based on the total weight of the finished catalyst. When evaluated in the epoxidation of butadiene as described hereinabove, the catalyst gives a conversion of 4.5% with a selectivity to 1,2-epoxy-3-butene of 94.1%. This example demonstrates that the thermal/decomposition procedure according to the prior art gives a catalyst which exhibits inferior activity.

COMPARATIVE EXAMPLE 5

Using the general procedure of Reference Example 1, alumina powder (10 g; Norton SN-06595) is impregnated using a solution of silver nitrate (3.4 g) in distilled water (50 mL). The mixture is agitated, the water is removed and the impregnated support is dried, all as described hereinabove. The catalyst precursor thus prepared is reduced according to the procedure of Examples 1-5 in a reduction gas consisting of 20 volume percent hydrogen in nitrogen using a gas hourly space velocity of 600 and a maximum reduction temperature of 400° C. to yield a catalyst containing 12.0 weight percent elemental silver. When evaluated in the epoxidation of butadiene as described hereinabove, the catalyst gives a conversion of 1.7% with a selectivity to 1,2-epoxy-3-butene of 80%. This example demonstrates that a catalyst prepared according to our invention but which does not contain an alkali metal promoter, exhibits inferior activity and selectivity.

The invention has been described in detail with particular reference to preferred embodiments thereof, but it will be understood that variations and modifications may be effected within the spirit and scope of the invention.

We claim:

1. A catalyst comprising a porous, refractory support having deposited thereon about 1 to 30 weight percent elemental silver and about 0.001 to 10 weight percent, based on the total weight of the catalyst, of a promoter selected from potassium, rubidium and cesium obtained by intimately contacting at a temperature of about 170° to 550° C. a catalyst precursor comprising a porous catalyst support material having deposited thereon a silver compound and a promoter selected from potassium, rubidium or cesium, with a gas comprising an inert gas containing about 4 to 50 volume percent hydrogen at a gas hourly space velocity of about 10 to 10,000.

2. A catalyst according to claim 1 comprising a porous, alumina support having deposited thereon about 2 to 20 weight percent elemental silver and about 0.01 to 2.0 weight percent, based on the total weight of the catalyst, of a promoter selected from rubidium or cesium obtained by intimately contacting over a temperature range of about 170° to 550° C. a catalyst precursor comprising a porous, alumina catalyst support material having deposited thereon a silver compound and a promoter selected from compounds of rubidium and cesium, with a gas comprising an inert gas containing about 4 to 50 volume percent hydrogen at a gas hourly space velocity of about 10 to 5000.

3. A catalyst according to claim 2 wherein the silver compound is silver nitrate and the promoter is cesium.

4. A catalyst according to claim 2 wherein the silver compound is silver nitrate and the promoter compound is cesium chloride.

5. A catalyst comprising a porous, refractory support having deposited thereon about 1 to 30 weight percent elemental silver and about 0.001 to 10 weight percent, based on the total weight of the catalyst, of a promoter selected from potassium, rubidium and cesium obtained from the process comprising the steps of:

(1) calcining at a temperature of about 250° to 350° C. a composition comprising a porous, refractory, catalyst support material having deposited thereon a silver compound and a promoter selected from compounds of potassium, rubidium and cesium in the presence of a gas flow; and (2) intimately contacting at a temperature of about 170° to 600° C. a calcined catalyst precursor obtained from step (1) with a flow of gas comprising an inert gas containing about 4 to 50 volume percent hydrogen.

6. A catalyst according to claim 5 comprising a porous, alumina support having deposited thereon about 2 to 20 weight percent elemental silver and about 0.01 to 2.0 weight percent, based on the total weight of the catalyst, of a promoter selected from rubidium or cesium obtained from the process comprising the steps of:
   (1) calcining at a temperature of about 250° to 350° C. a composition comprising a porous, refractory, catalyst support material having deposited thereon a silver compound and a promoter selected from compounds of rubidium and cesium in the presence of a flow of a gas selected from air, oxygen-depleted air, an inert gas and a mixture thereof at a gas hourly space velocity of about 10 to 5000; and
   (2) intimately contacting over a temperature range of about 170° to 550° C. a calcined catalyst precursor obtained from step (1) with a flow of gas comprising an inert gas containing about 4 to 50 volume percent hydrogen at a gas hourly space velocity of about 10 to 5000.

7. A catalyst according to claim 6 wherein the silver compound is silver nitrate and the promoter is cesium.

8. A catalyst according to claim 6 wherein the silver compound is silver nitrate and the promoter compound is cesium chloride.

9. Process for the preparation of a catalyst comprising a porous, refractory support having deposited thereon about 1 to 30 weight percent elemental silver and about 0.001 to 10 weight percent, based on the total weight of the catalyst, of a promoter selected from potassium, rubidium and cesium which comprises intimately contacting at a temperature of about 170° to 500° C. a catalyst precursor comprising a porous catalyst support material having deposited thereon a silver compound and a promoter selected from potassium, rubidium or cesium, with a gas comprising an inert gas containing 4 to 50 volume percent hydrogen at a gas hourly space velocity of about 10 to 10,000.

10. Process according to claim 9 for the preparation of a catalyst comprising a porous, alumina support having deposited thereon about 2 to 20 weight percent elemental silver and about 0.01 to 2.0 weight percent, based on the total weight of the catalyst, of a promoter selected from rubidium or cesium which comprises intimately contacting over a temperature range of about 170° to 500° C. a catalyst precursor comprising a porous, alumina catalyst support material having deposited thereon a silver compound and a promoter selected from compounds of rubidium and cesium, with a gas comprising an inert gas containing about 4 to 50 volume percent hydrogen at a gas hourly space velocity of about 10 to 5000.

11. A process for the preparation of a catalyst comprising a porous, refractory support having deposited thereon about 1 to 30 weight percent elemental silver and about 0.001 to 10 weight percent, based on the total weight of the catalyst, of a promoter selected from potassium, rubidium and cesium which comprises the steps of:
   (1) calcining at a temperature of about 250° to 350° C. a composition comprising a porous, refractory, catalyst support material having deposited thereon a silver compound and a promoter selected from compounds of potassium, rubidium and cesium in the presence of a gas flow; and
   (2) intimately contacting at a temperature of about 170° to 600° C. a calcined catalyst precursor obtained from step (1) with a flow of gas comprising an inert gas containing about 4 to 50 volume percent hydrogen.

12. A process for the preparation of a catalyst comprising a porous, alumina support having deposited thereon about 2 to 20 weight percent elemental silver and about 0.01 to 2.0 weight percent, based on the total weight of the catalyst, of a promoter selected from rubidium or cesium which comprises the steps of:
   (1) calcining at a temperature of about 250° to 350° C. a composition comprising a porous, refractory, catalyst support material having deposited thereon a silver compound and a promoter selected from compounds of rubidium and cesium in the presence of a flow of a gas selected from air, oxygen-depleted air, an inert gas and a mixture thereof at a at a gas hourly space velocity of about 10 to 5000; and
   (2) intimately contacting over a temperature range of about 170° to 550° C. a calcined catalyst precursor obtained from step (1) with a flow of gas comprising an inert gas containing about 4 to 50 volume percent hydrogen at a gas hourly space velocity of about 10 to 5000.

* * * * *

UNITED STATES PATENT AND TRADEMARK OFFICE
CERTIFICATE OF CORRECTION

PATENT NO. : 5,081,096
DATED : January 14, 1992
INVENTOR(S) : John R. Monnier and Peter J. Muehlbauer It is certified that error appears in the above-identified patent and that said Letters Patent is hereby corrected as shown below:

Column 13, line 19 (Claim 6, line 16), "550°C." should be ---500°C.---

Column 14, line 42 (Claim 12, line 16), "550°C." should be ---500°C.---

Signed and Sealed this

Thirtieth Day of March, 1993

Attest:

STEPHEN G. KUNIN

*Attesting Officer*　　　*Acting Commissioner of Patents and Trademarks*